United States Patent [19]

Lewis

[11] Patent Number: 4,992,573

[45] Date of Patent: Feb. 12, 1991

[54] RHODIUM COLLOID, METHOD OF MAKING, AND USE

[75] Inventor: Larry N. Lewis, Scotia, N.Y.

[73] Assignee: General Electric Company, Schenectady, N.Y.

[21] Appl. No.: 508,622

[22] Filed: Apr. 13, 1990

Related U.S. Application Data

[62] Division of Ser. No. 177,717, Apr. 5, 1988, Pat. No. 4,946,818.

[51] Int. Cl.$^5$ .............................. C07F 7/08; C07F 7/18
[52] U.S. Cl. ...................................... 556/479; 556/450; 556/451; 556/453; 556/460; 556/461; 556/462
[58] Field of Search ............... 556/479, 450, 451, 453, 556/460, 461, 462

[56] References Cited

U.S. PATENT DOCUMENTS

| | | | |
|---|---|---|---|
| 3,296,291 | 1/1967 | Chalk et al. | 556/479 X |
| 3,546,266 | 12/1970 | Coffey | 556/479 X |
| 4,064,154 | 12/1977 | Chandra et al. | 556/479 X |
| 4,681,963 | 7/1987 | Lewis | 556/479 X |
| 4,831,081 | 5/1989 | King et al. | 556/479 X |

FOREIGN PATENT DOCUMENTS

| | | | |
|---|---|---|---|
| 0036425 | 9/1974 | Japan | 556/479 |
| 0732268 | 5/1980 | U.S.S.R. | 556/479 |

Primary Examiner—Paul F. Shaver
Attorney, Agent, or Firm—William A. Teoli; James C. Davis, Jr.; William H. Pittman

[57] ABSTRACT

A rhodium colloid has been found to be a superior catalyst for the hydrosilylation of silicon hydride having two or three hydrogens attached to silicon. The rhodium colloid is made by effecting reaction between rhodium trichloride and certain silicon hydride.

2 Claims, No Drawings

RHODIUM COLLOID, METHOD OF MAKING, AND USE

This is a division of Ser. No. 177,717, filed Apr. 5, 1988, now U.S. Pat. No. 4,946,818.

BACKGROUND OF THE INVENTION

The present invention relates to a rhodium colloid which is useful as a hydrosilylation catalyst for silicon hydride having two or three hydrogen atoms attached to silicon. More particularly, the present invention relates to the reaction of rhodium trichloride with certain silicon hydride to produce a rhodium colloid.

Prior to the present invention as shown by Lewis, U.S. Pat. No. 4,681,963, platinum colloids were found to be superior hydrosilylation catalysts for effecting the addition of silicon hydride to an olefin including vinyl silicon materials. In certain situations however, particularly where a poly-addition reaction was necessary such as when using a silicon hydride having more than one hydrogen atom attached to silicon such as two or three hydrogen atoms, the employment of the platinum colloids was less effective. As a result, it was difficult to effect addition between silicon polyhydrides such as $C_6H_{13}SiH_3$ to olefins such as 1-octene to make tetraalkyl-substituted silanes useful as hydraulic fluids and lubricants.

Silahydrocarbons have been made by the use of a rhodium-containing catalyst having a triphenylphosphine ligand as shown by Onepchenko et al., U.S. Pat. No. 4,572,791. Although the silahydrocarbons can be made by the Onepchenko et al. method, it requires an expensive catalyst, such as chloro(tristriphenylphosphine)rhodium(I) and the hydrosilylation reaction must be performed under a nitrogen atmosphere. Another hydrosilylation procedure utilizing a rhodium catalyst is shown by Chalk et al., U.S. Pat. No. 3,296,291. Chalk et al. utilizes an aliphatic alcohol to solubilize the rhodium chloride prior to contacting it with the silicon hydride reactant or the olefin reactant during the hydrosilylation procedure. Although effective results are achieved by the Chalk et al. method, reduced silahydrocarbon yields can result because the aliphatic alcohol can react directly with the silicon hydride before it has a chance to react with the olefin. It would be desirable, therefore, to provide a method for making silahydrocarbon based on the use of polyhydric silicon materials in combination with olefins without the use of expensive catalyst or reactants or conditions which render the procedure economically unattractive.

The present invention is based on my discovery that rhodium trichloride can be reacted under ambient conditions directly with silicon hydride having no more than two monovalent hydrocarbon radicals attached to silicon to produce a rhodium colloid which exhibits superior effectiveness as a hydrosilylation catalyst under ambient conditions with silicon hydride having two or three hydrogen atoms attached to silicon.

STATEMENT OF THE INVENTION

There is provided by the present invention, a rhodium colloid comprising the reaction product of from 10 to about 100 moles of silicon hydride, per mole of rhodium trichloride, where the silicon hydride has a boiling point of at least 25° C. at atmospheric pressure, and the silicon hydride has from 1 to 3 hydrogen atoms attached to silicon and at least 1, and up to 3 monovalent radicals, other than hydrogen, selected from 1 or 2 $C_{(1-13)}$ hydrocarbon radicals, and 1 to 3 $C_{(1-8)}$ ethoxy, siloxy, halogen and mixtures of such monovalent radicals.

The rhodium trichloride which can be used in the practice of the present invention to make the hydrosilylation catalyst is solid $RhCl_3 \times H_2O$ containing from 39–49% Rh by weight, more typically 40% rhodium.

Among the silicon hydride which can be used in the practice of the present invention to make the rhodium colloid are, silicon hydride having the formula, $$R_a(R^1)_b SiH_{(4-a-b)},\qquad(I)$$

where R is a monovalent radical selected from $C_{(1-13)}$ monovalent hydrocarbon radicals, and $C_{(1-13)}$ monovalent hydrocarbon radicals substituted with radicals inert during hydrosilylation, $R^1$ is selected from $C_{(1-8)}$ alkoxy radicals, siloxy, halogen or mixtures thereof, a is a whole number equal to 0 to 2 inclusive, b is a whole number equal to 0 to 3 inclusive and the sum of a and b is equal to 1 to 3 inclusive.

Radicals included by R of Formula (I) are, for example, alkyl radicals such as methyl, ethyl, propyl, butyl, pentyl and hexyl; aryl radicals such as phenyl, xylyl, phthalyl, chlorophenyl and bromophthalyl. Radicals included by $R_1$ are, for example, chloro, bromo, iodo, fluoro, methoxy and ethoxy.

Among the silicon hydride of Formula (I), there are included, for example, triethoxysilane, dimethylethoxysilane, 1,2-tetramethyldisiloxane, 1,3,5,7-tetramethylcyclotetrasiloxane, trichlorosilane, methyldiethoxysilane and methyldecylsilane.

In a further aspect of the present invention there is provided a hydrosilylation method comprising effecting reaction between an olefinically unsaturated material, and a silicon hydride having up to three chemically combined hydrogen atoms, per silicon atom, in the presence of an effective amount of a hydrosilylation catalyst comprising a rhodium colloid as previously defined.

The olefinically unsaturated materials which can be used in the practice of the hydrosilylation method of the present invention include organic materials such as $R-CH=CH_2$ where R is a $C_{(1-13)}$ monovalent organic radical selected from alkyl such as methyl, ethyl, propyl, isopropyl, butyl, octyl, dodecyl; cycloalkyl such as cyclopentyl, cyclohexyl; aryl such as phenyl, naphthyl, tolyl, xylyl; aralkyl such as benzyl, phenyl ethyl; and halogenated derivatives such as chloromethyl, trifluoromethyl, etc.

Some of the olefinically unsaturated materials which can be used are, for example, 1-hexene, 1-octene, 1-decene and vinylcyclohexene. Diolefin also can be used such as 1,4-butadiene, 1,5-pentadiene and 1,6-hexadiene.

Olefinically unsaturated organosilicon materials also can be used such as vinylpentamethyldisiloxane, 1,3-divinyltetramethyldisiloxane, 1,1,3-trivinyltrimethyldisiloxane, 1,1,3,3-tetravinyldimethyldisiloxane, as well as higher polymers containing up to 100,000 or more silicon atoms per molecule.

Also included within the scope of the olefinically unsaturated organopolysiloxanes are cyclic materials containing silicon-bonded vinyl or allyl radicals, such as the cyclic trimer, tetramer or pentamer of methylvinylsiloxane or methyl allylsiloxane. Among these cyclic materials, tetramethyltetraallylcyclotetrasiloxane and tetramethyltetravinylcyclotetrasiloxane are preferred.

A preferred class of vinylorganopolysiloxane which can be used in the practice of the present invention are those shown by Modic in U.S. Pat. No. 3,436,366, incorporated herein by reference. These compositions comprise (1) 100 parts by weight of a liquid vinyl chainstopped polysiloxane having the formula,

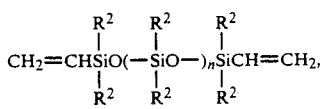

where $R^2$ is selected from the same or different monovalent hydrocarbon radicals free of aliphatic unsaturation, with at least 50 mole percent of the $R^2$ groups being methyl, and where n has a value sufficient to provide a viscosity of from about 50,000 to 750,000 centistokes at 25° C., preferably from about 50,000 to 180,000, and (2) from 20 to 50 parts by weight of an organopolysiloxane copolymer comprising $(R^3)_3SiO0.5$ units and $SiO_2$ units, where $R^3$ is a member selected from the class consisting of vinyl radicals and monovalent hydrocarbon radicals free of aliphatic unsaturation, where the ratio of $(R^3)_3SiO0.5$ units to $SiO_2$ units is from about 0.1:1 to 1:1, and where from about 2.5 to 10 mole percent of the silicon atoms contain silicon-bonded vinyl groups.

In addition to the silicon hydride of formula (1), there also can be used in the practice of the hydrosilylation method of the present invention organopolysiloxane and cyclopolysiloxane having chemically combined ≡SiH units.

Hydrosilylation can be conducted at temperatures in the range of from 20° C. to 125° C. There can be used from 0.1 to 10 moles of olefin per mole of silicon hydride. An effective amount of the hydrosilylation catalyst is from about 5 parts per million of rhodium colloid to 200 parts per million of rhodium colloid based on the weight of the hydrosilylation mixture. Although the order of addition of reactants is not critical, one procedure which has been found effective is to add the silicon hydride to a mixture of the rhodium chloride and olefin along with a minor amount of the silicon hydride. The resulting mixture can thereafter be heated with stirring.

In order that those skilled in the art will be better able to practice the present invention, the following examples are given by way of illustration and not by way of limitation. All parts are by weight.

EXAMPLE 1

A mixture of 9 milligrams or 100 parts per million rhodium trichloride hydrate, 23.87 grams (0.215 mole) of 1-octene and two drops of methyldecylsilane was heated, with stirring, at 85° C. The mixture turned to a yellow-brown color. There was then slowly added to the mixture, with stirring, 10 grams (0.0538 mole) of methyl(decyl)silane for a period of 1 hour, producing a temperature of 107° C. The mixture was then analyzed, after additional stirring, by gas chromatography which showed a complete conversion to a mixture of methyldecyldioctylsilane and methyldecyloctyloctenylsilane. The results were confirmed by proton NMR.

The above reaction was repeated except that 100 ppm. of Pt was used (66 μL. of a 5% xylene solution) in place of $RhCl_3 \times H_2O$. The platinum catalyst used is shown by Karsteadt, U.S. Pat. No. 3,775,452. Analysis of GC after 1 hour showed the presence of 1-octene but there was no evidence of silahydrocarbon.

A further comparison was made between the above Karstead catalyst and a rhodium colloid made in accordance with the present invention having 0.2% by weight Rh based on elemental analysis. The reaction was run at room temperature and it involved the hydrosilylation of vinyltrimethylsilane with diethylsilane. The following results were obtained:

| Rh (50 ppm) | | Pt (100 ppm) | |
| --- | --- | --- | --- |
| Time (min.) | % Conversion | Time (min.) | % Conversion |
| 4 | 19.7 | 11 | 4.6 |
| 151 | 78.4 | 167 | 26.8 |
| | | 1643 | 78.1 |

The above results show that the rhodium colloid was superior to the platinum catalyst when adding a dihydride to a vinylsilane.

EXAMPLE 2

There was slowly added 0.1 gram of rhodium trichloride hydrate to 5 mL. of dimethylethoxysilane. Hydrogen evolution commenced immediately and the initially colorless solution turned yellow and finally red. Analysis by $^{29}$ silicon NMR and GCMS of the resulting silicon-containing products showed a siloxane mixture which was mainly octamethylcyclotetrasiloxane. Elemental analysis showed that the solution contained 0.15% rhodium. Transmission electron microscopy showed the presence of 20 angstroms diameter rhodium crystallites.

A rhodium catalyst was also prepared in accordance with Chalk et al., U.S. Pat. No. 3,296,291 by reaction of an ethanol solution of rhodium trichloride with triethylsilane.

A hydrosilylation reaction mixture of equimolar amounts of triethoxysilane and vinyl trimethylsilane was prepared utilizing initially 20 parts per million of the rhodium trichloride catalyst. The catalyst was made in accordance with the practice of the present invention (Lewis) and Chalk et al. The reaction was conducted under ambient conditions at room temperature. It was found that little or no reaction occurred with the Chalk et al. catalyst. It was therefore decided to enhance the concentration of the Chalk et al. catalyst to 100 parts per million while maintaining the concentration of the Lewis catalyst at 20 parts per million. The following results were obtained.

| Chalk | | Lewis | |
| --- | --- | --- | --- |
| Time (min.) | % Conversion | Time (min.) | % Conversion |
| 6 | 5 | 11 | 14.6 |
| 36 | 6 | 41 | 18.4 |
| 80 | 13.2 | 84 | 24.9 |
| 124 | 20.8 | 127 | 29.1 |
| 158 | 20.3 | 169 | 41 |
| 275 | 56.2 | 285 | 55.5 |

The above was repeated and measured for % conversion after 5 hours. The Lewis catalyst was found to be more active: Lewis (50%) Chalk (15.1%).

The above results show that the Lewis catalyst is a superior hydrosilylation catalyst as compared to Chalk et al. even at a concentration one-fifth of the Chalk et al. catalyst.

EXAMPLE 3

There was added 40 grams of methyldecylsilane for a period of 25 minutes to a mixture of 95.5 parts of 1-octene and 8 parts per million of rhodium catalyst as prepared in Example 2. A slow stream of air bubbled into the solution prior to the addition of the methyldecylsilane. The octene solution containing the rhodium catalyst was also preheated to a temperature of 80° C. After an additional 30 minutes of heating, an additional amount of rhodium catalyst was added to the mixture for a final total of 17 parts per million. After ½ hour, a quantitative yield of methyldecyldioctylsilane was obtained.

EXAMPLE 4

A mixture of 49 microliters of rhodium colloid as prepared in Example 2 was combined with 18 ml. of 1-octene. There was added to the mixture a solution at about 70° C. of 28 ml. of 1-octene and 7 ml. of hexylsilane. During the addition, air was blown into the reaction mixture over the course of an hour. Analysis by GCMS showed that all of the hexylsilane was consumed. Proton NMR showed that all of the silicon hydride was gone and that alkyl resonances consistent with hexyltrioctylsilane were present. The $^{29}$ silicon NMR showed a single resonance at $-1.3$ parts per million consistent with a tetraalkylsilane.

EXAMPLE 5

The procedure of preparing the rhodium catalyst of Example 2 was repeated except triethoxysilane was used in place of dimethylethoxysilane. Substantially the same catalyst and siloxane results were achieved.

In addition, rhodium colloid was also formed as in Example 2 when tetramethyldisiloxane was used as the silicon hydride source.

Although the above examples are directed to only a few of the very many variables both with respect to ingredients and conditions which can be used in the practice of the present invention, it should be understood that the present invention is directed to a much broader variety of materials, as well as conditions, as shown in the description preceding these examples.

What is claimed and sought to be protected by Letters Patent of the United States is as follows:

1. A hydrosilylation method comprising effecting reaction between a silicon hydride having up to 3 chemically combined hydrogen atoms per silicon atom and an olefinically unsaturated material in the presence of an effective amount of a hydrosilylation catalyst comprising a rhodium colloid resulting from the reaction of from 10 to about 100 moles of a silicon hydride, per mole of rhodium trichloride, where the silicon hydride has a boiling point of at least 25° C. at atmospheric pressure and the silicon atom of the silicon hydride is satisfied with from 1 to 3 hydrogen atoms and at least 1, and up to 3 monovalent radicals, other than hydrogen, selected from 1 or 2 $C_{(1-13)}$ hydrocarbon radicals and 1 to 3 $C_{(1-8)}$ alkoxy, siloxy, halogen and mixtures of such monovalent radicals.

2. A hydrosilylation method in accordance with claim 1, where the olefinically unsaturated material is 1-octene.

* * * * *